United States Patent [19]

Broadwin et al.

[11] Patent Number: 4,931,047

[45] Date of Patent: Jun. 5, 1990

[54] METHOD AND APPARATUS FOR PROVIDING ENHANCED TISSUE FRAGMENTATION AND/OR HEMOSTASIS

[75] Inventors: Alan Broadwin, Brooklyn, N.Y.; Charles Vassallo, Oxford, Conn.; Joseph N. Logan, Trumbull, Conn.; Robert W. Hornlein, Stamford, Conn.

[73] Assignee: Cavitron, Inc., Stamford, Conn.

[21] Appl. No.: 103,022

[22] Filed: Sep. 30, 1987

[51] Int. Cl.$^5$ .................. A61B 17/32; A61B 17/39
[52] U.S. Cl. .................................. 604/22; 604/35; 606/42; 606/45; 606/49; 606/169
[58] Field of Search .............. 604/22, 35; 128/24 A, 128/303 R, 303.14, 303.17, 305; 606/42, 45, 48, 49, 50, 169–171

[56] References Cited

U.S. PATENT DOCUMENTS

| | | | |
|---|---|---|---|
| 2,714,890 | 8/1955 | Vang | 128/24 A |
| 3,589,363 | 6/1971 | Banko et al. | 128/276 |
| 3,636,943 | 1/1972 | Balamuth | 128/24 |
| 3,693,613 | 9/1972 | Kelman | 128/24 |
| 3,815,604 | 6/1974 | O'Malley et al. | 604/22 |
| 4,063,557 | 12/1977 | Wuchinich et al. | 128/276 |
| 4,378,801 | 4/1983 | Oosten | 128/303 |
| 4,552,143 | 11/1985 | Lottick | 128/303.14 |
| 4,562,838 | 1/1986 | Walker | 128/303.14 |
| 4,674,498 | 6/1987 | Stasz | 128/303 |
| 4,747,820 | 5/1988 | Hornlein et al. | 604/22 |
| 4,750,902 | 6/1988 | Wuchinich et al. | 604/22 |

FOREIGN PATENT DOCUMENTS 8701276 3/1987 PCT Int'l Appl.
8706116 10/1987 PCT Int'l Appl.

Primary Examiner—Lee S. Cohen
Attorney, Agent, or Firm—Vorys, Sater, Seymour & Pease

[57] ABSTRACT

An apparatus having a vibratable tip for ultrasonically disintegrating tissue in a surgical procedure and for aspirating the disintegrated tissue and fluids away from the surgical site through an opening in the tip. A connection to an electrosurgical unit provides for delivery of RF cutting current, RF coagulating current or a blend thereof to the tip so that electrosurgical procedures can be conducted separately or simultaneously with ultrasonic aspiration through the tip. It thus is now possible, for example, to electrocauterize simultaneously with ultrasonic fragmentation with a single handheld surgical device. The simultaneous delivery of ultrasonic vibrations and RF current to the tip also has been found to increase the tissue fragmentation rate.

54 Claims, 3 Drawing Sheets

METHOD AND APPARATUS FOR PROVIDING ENHANCED TISSUE FRAGMENTATION AND/OR HEMOSTASIS

BACKGROUND OF THE INVENTION

The present invention relates to surgical methods and apparatuses for ultrasonically fragmenting and aspirating, and electrosurgically coagulating and electrosurgically cutting tissue at an operative site on a patient.

The application of ultrasonically vibrating surgical devices used to fragment and remove unwanted tissue with significant precision and safety has led to the development of a number of valuable surgical procedures, and the use of ultrasonic aspirators for the fragmentation and surgical removal of tissue from a body has become well known. Initially, the technique of surgical aspiration was applied for the fragmentation and removal of cataract tissue as shown, for example, in U.S. Pat. Nos. 3,589,363 and 3,693,613; the contents of these patents and each of the other patents and documents mentioned herein are hereby incorporated by reference in their entirety. Later, such techniques were applied with significant success to neurosurgery and other surgical specialties where the application of ultrasonic energy through a small, handheld device for selectively removing tissue on a layer-by-layer basis with precise control has proven feasible. Recently an ultrasonic aspirator for the endoscopic removal of compliant biological tissue as described in International Publication No. WO 87/01276 has become known.

Certain devices known in the art characteristically produce continuous vibrations having a substantially constant amplitude at a frequency of about twenty to about thirty KHz up to about forty to about fifty KHz. U.S. Pat. No. 3,589,363 describes one such device which is especially adapted for use in the removal of cataracts, while U.S. Pat. No. 4,063,557 describes a device suitable for removal of soft tissue which is particularly adapted for removing highly compliant elastic tissue mixed with blood. Such devices are continuously operative when the surgeon wishes to fragment and remove tissue, and generally operate under the control of a foot switch.

One known instrument for ultrasonically fragmenting tissue at an operative site and then aspirating the tissue particles and fluid away from the site is the CUSA Model System 200 ultrasonic aspirator which is manufactured and sold by Cavitron Surgical Systems of Stamford, Conn.; see also U.S. Ser. No. 847,301. When the longitudinally oscillating metallic tip thereof is contracted with tissue it gently, selectively and precisely fragments and removes the tissue. Some of the advantages of this unique surgical instrument are that there is little resulting damage to healthy tissue in a tumor removal procedure, blood vessels can be skeletonized, healing of tissue is promoted, no charring or tearing of margins of surrounding tissue results, only minimal pulling of healthy tissue is experienced, and excellent tactile feedback for selectively controlled tissue fragmentation and removal is provided.

Surgeons using the CUSA ultrasonic surgical instrument have indicated a desire for additional and improved capabilities for this instrument. In particular they have requested provisions for controlled penetration of capsular membranes without damage to the organs, precise and rapid removal of fibrous tissue structures such as in mucosal proctectomy procedures, and an increased rate of tissue fragmentation and removal. During many surgical procedures wherein ultrasonic fragmentation instruments have been employed additional instruments have been required for tissue cutting and hemostasis at the surgical site. Hemostasis is needed for example in desiccation techniques for deep coagulation to dry out large volumes of tissue and also in fulguration techniques for spray coagulation to dry out the surfaces of tissues. See, e.g. U.S. Pat. No. 4,378,801. Often an electrosurgical pencil plugged into an electrosurgical unit for tissue cutting and hemostasis and a suction probe for aspiration of fluids and cut tissue particles are used. Since many surgical tools are thereby required at a single surgical site, the total surgical time is increased, and efficiency decreased, as the surgeon must switch among different instruments. Also, undesirable amounts of blood are lost because of the time needed to switch from a cutting or fragmenting tool to a cauterizing instrument when bleeding is observed. Additionally, by simultaneously maintaining a plurality of surgical devices at the operative site the surgeon's field of view is reduced. Further due to the complexity of the procedures false activation of the electrosurgical pencil when not in use causing an RF burning of the patient can occur, and meet the desires and needs of the surgeons.

Accordingly, a need has arisen for improved surgical procedures and apparatuses which remedy these problems, and meet the above-expressed desires and needs of the surgeons.

SUMMARY OF THE INVENTION

The present invention remedies these problems by incorporating RF coagulating and RF cutting capabilities to the vibratable tip of an ultrasonic fragmenting and aspiration device. Surprisingly not only are the fragmentation and aspiration capabilities not diminished they are actually enhanced by the delivery of RF energy to the fragmentation and aspiration tip. A switching mechanism conveniently accessible to the surgeon allows him during the surgery and with the instrument tip at the surgical site to instantly switch among the application of no function, one function, or the simultaneous application of any combination of functions of the instrument thereby increasing the efficacy and decreasing the time of the surgery. The bleeding which occurs during the tissue fragmentation is more quickly and better controlled. Provision for controllable and delivery of irrigating and cooling fluids to the surgical site via the instrument is also made.

Other objects and advantages of the present invention will become apparent to those persons having ordinary skill in the art to which the present invention pertains from the foregoing description taken in conjunction with the accompanying drawings.

DETAILED DESCRIPTION OF THE PREFERRED EMBODIMENTS

Figure 1:
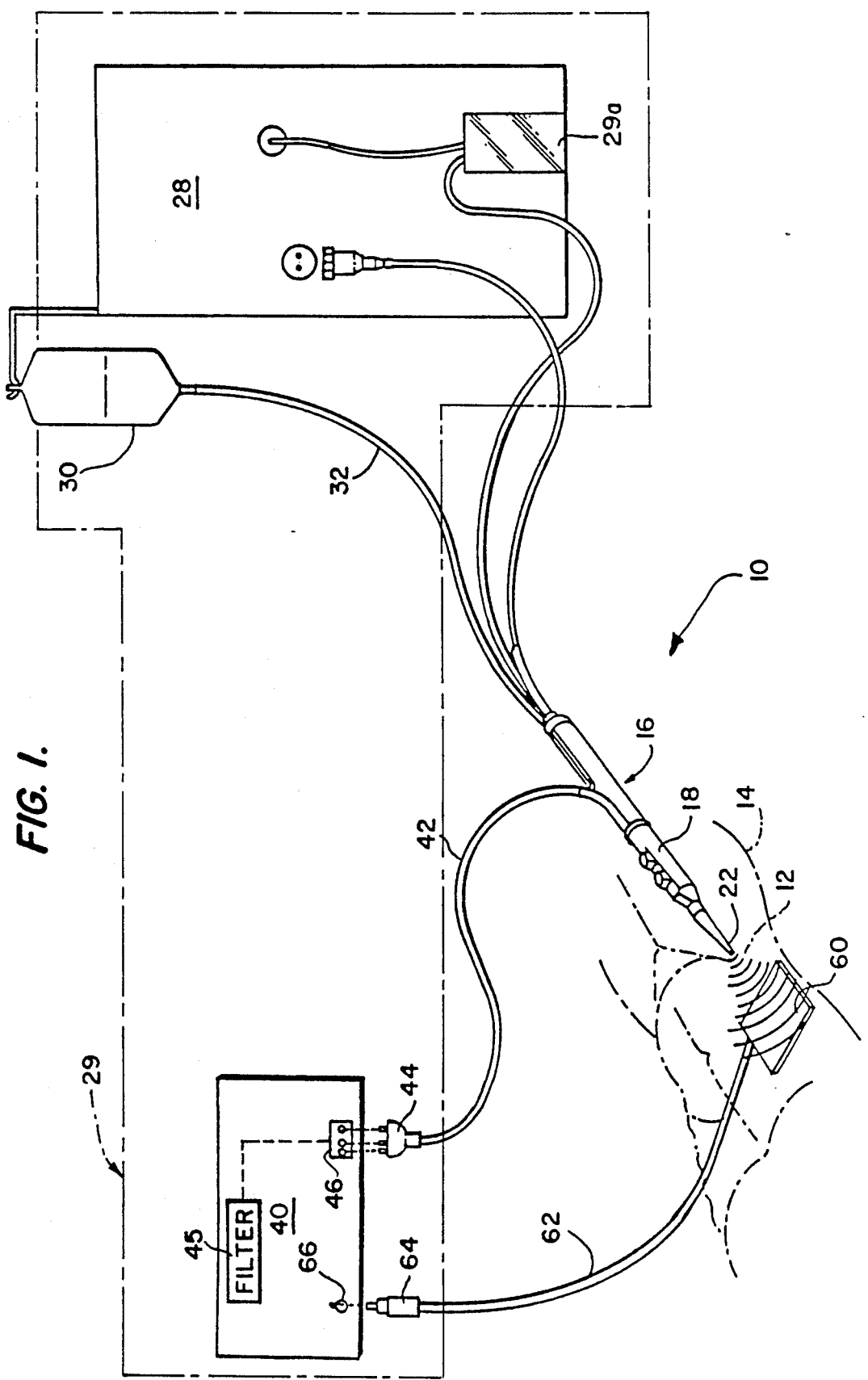
FIG. 1 illustrates a surgical system of the present invention.

A surgical system of the present invention is illustrated in FIG. 1 generally at 10 performing a surgical procedure at a surgical site 12 on a patient 14. System 10 includes a handpiece shown generally at 16 which, as will described hereinafter in detail, is capable of performing ultrasonic fragmentation, aspiration, electrosurgical cutting, fluid irrigation, and electrosurgical coagulation or hemolysis functions on tissue at the surgical site 12. These functions can be performed either separately or simultaneously in any combination. The handpiece 16 can be a known ultrasonic fragmentation handpiece such as the previously-mentioned CUSA handpiece or that described in the Wuchinich et al U.S. Pat. No. 4,063,557, modified to include electrosurgical cutting and coagulating functions as explained hereinafter. These modifications can be built into the handpiece itself, or provided as part of a disposable or replaceable handpiece component such as on the manifold or nosecone thereof.

Figure 3:
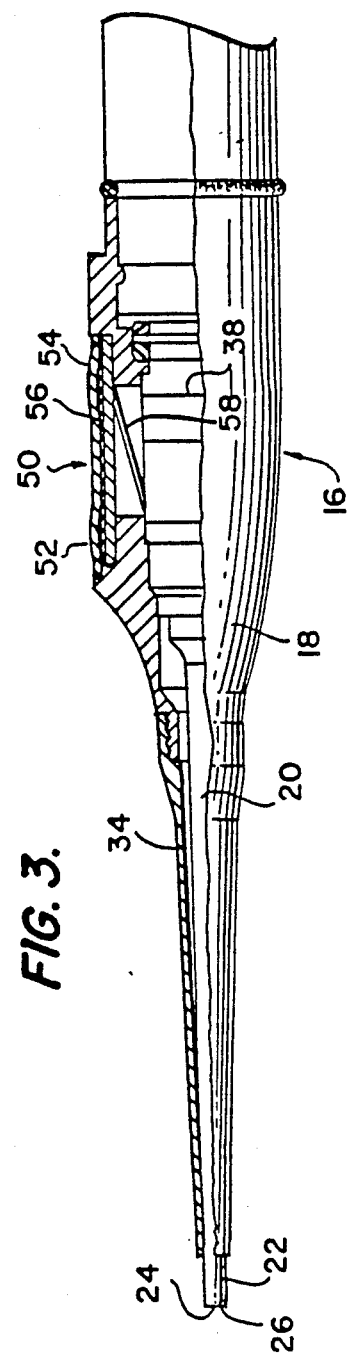
FIG. 3 is a side view in partial cross section of the forward portion of the first handpiece of FIG. 2.
Figure 6:
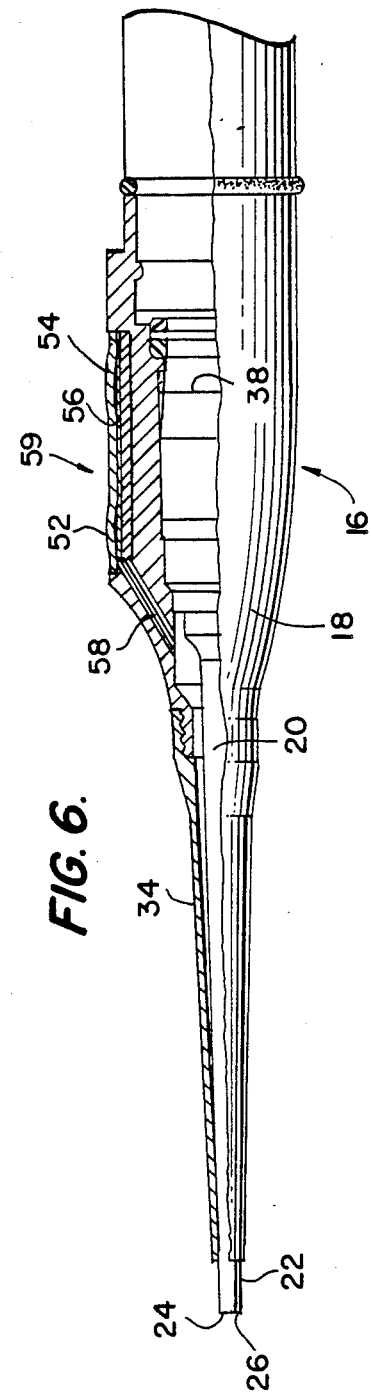
FIG. 6 is a side view in partial cross section of the forward portion of the second handpiece of FIG. 5.

Handpiece 16 as shown in FIG. 1 includes a housing 18 sized and configured to be easily and comfortably gripped and manipulated by the surgeon's hand. An elongated tapered ultrasonically-vibratable tool 20 is supported by the housing, as seen in FIGS. 3 and 6, and disposed in a forwardly direction so that the tool tip 22 thereof extends forwardly a distance out from the housing and has a tip opening 24 at its distal end. The tool 20 is hollow and defines a longitudinal tool passageway 26 therethrough.

An aspiration pump housed for example in a housing 28 can apply a suction pressure through tube 29 to the proximal end of the passageway 26 so that tissue particles, blood, fluids and the like at the surgical site 12 can be aspirated from the surgical site 12 in through tip opening 24 out through passageway 26 towards the console or housing 28 and into a suitable suction container 29a.

One of the fluids which may be aspirated from the surgical site is a saline irrigation fluid provided thereto as part of the surgical procedure as for example to provide a suspension fluid for the tissue particles fragmented by the handpiece 16. The saline irrigation solution can gravity drain in a known manner from a bottle or bag 30 suspended above the surgical site 12 through an irrigation tubing 32 to and into the handpiece 16. It then flows through an annular passage 34 defined between the tool 20 and housing or forward manifold position thereof and then out the housing around the tool tip 22 to the surgical site 12. In addition to supplying irrigation fluid to the surgical site 12, the fluid cools the vibrating tip 22 and the blood, tissue particles and other aspirated material to prevent the tool 20 from being damaged and to slow down the coagulation of the blood. By wetting the tissue aspiration is thereof is aided and adjacent healthy tissue is protected from damage. Where the surgical site 12 is an enclosed or semi-enclosed area such as the eye in ultrasonic cataract removal procedures, it is important to maintain a pressure therein within a certain range, and flow control systems for maintaining such pressures are known, and can be used herein. See e.g. U.S. Pat. No. 3,693,613. Control of the delivery of irrigating fluid, and application of aspiration suction pressure and ultrasonic energy can be by a footswitch readily accessible to the surgeon as is known in the art.

The tool 20 is ultrasonically vibrated by an resonant vibrating system shown generally at 38 and mounted in the handpiece 16. The system 38 includes a transducer, such as a magnetostrictive stack as taught in Re. 25,033 and an ultrasonic mechanical transformer to vary the stroke caused by the transducer. The tool 20 itself comprises a substantially unitary body having a male threaded end designed for replacement as required and attached to a connecting member of the vibrating system 38. The vibrating system 38 causes the tip 22 to vibrate ultrasonically with a stroke in excess of 0.001 inch and preferably 0.014 inch and at a frequency range of 20 KHz-50 KHz and preferably 23 KHz-37 KHz.

Figure 2:
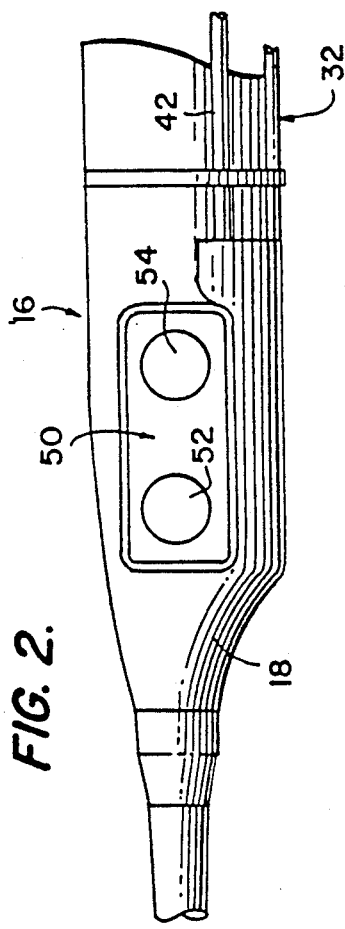
FIG. 2 is a top view of a central portion of a first handpiece of the system of FIG. 1.
Figure 4:
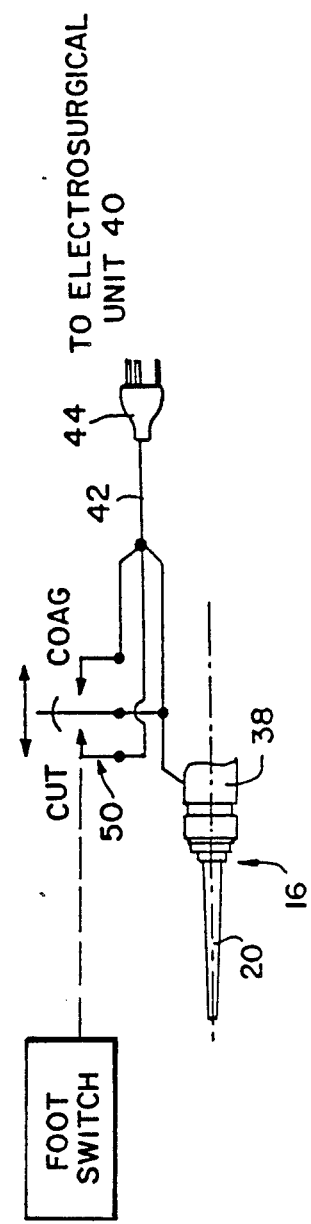
FIG. 4 is a side view of the forward portion of the first handpiece of FIG. 2 illustrating in schematic form an RF switching mechanism therefor.

The electrosurgical unit (ESU), such as a free standing hospital unit shown generally at 40 or as discussed in U.S. Pat. Nos. 3,898,991, 3,963,030 and 4,051,855 provides the RF energy for the handpiece 16. It is also within the scope of this invention to design and secure the electrosurgical unit 40 within the housing 28 together with the aspirator pump in a single preferably portable unit 29. The ESU 40 generates RF energy and a cautery cable 42 is operatively connected at one end to the handpiece 16 and has a plug 44 at its other end adapted to be plugged into the handswitch active jack 46 of the ESU 40 to deliver the RF energy to the handpiece 16. The electrosurgical unit (ESU) which provides the RF current includes any known type of electrical filtering device 45 for preventing malfunction of the logic controls in the ESU when coupled to the tool tip and the ESU is activated. A switch assembly positioned so as to conveniently actuated by the surgeon as he manipulates the handpiece 16 allows him to control the delivery of RF energy from the ESU 40 to the tool 20. The switch assembly can allow the surgeon to select among "no" RF energy, RF coagulating energy, RF cutting energy, or a simultaneous blend of coagulating and cutting signal energies. RF cutting and coagulating currents differ and are defined as pure sine wave and damped sine wave, respectively. The switch assembly can be a footswitch (FIG. 4) or a handswitch and if a handswitch securable on the handpiece 16 to be accessible and actuatable by the surgeon's hand (forefinger) as it holds and manipulates the handpiece 16. A handpiece handswitch can be integrally formed with or built into the handpiece 16 so to be totally reusable, or as a separable and replaceable unit such as an add-on switch assembly or to a separable handpiece manifold; this manifold can comprise a portion of the irrigation fluid passageway as well. Different manifold configurations are shown for example in PCT/US87/00795. Many switch assemblies such as push button, rocker or slide constructions can be used. A first preferred switch assembly construction is shown in the drawings in FIGS. 2-3 generally at 50. It can be a push button, single pole double (SPDT) normally open switch, as shown schematically in FIG. 4, permitting keying of "cut" or "coag" modes of RF current from the ESU 40. Once selected as through the "cut" mode or "coag" mode dome switches, 52, 54, respectively, the RF current is caused by circuit board 56 to flow from the ESU 40 through the interfacing or cautery cable 42 to a metallic contactor 58 through an electrical connector to the tip. An alternative control/delivery of RF energy would be to provide a single push button (blend) on the handpiece and controlled by a single continuously variable control calibrated on its lower limit to cut and to coag on its upper limit.

Figure 5:
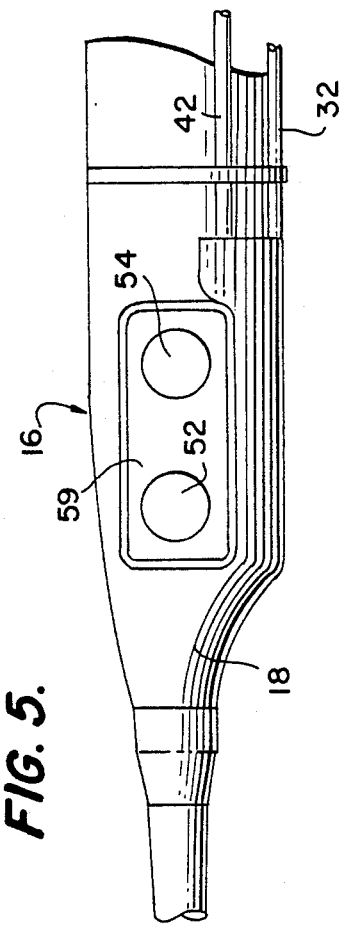
FIG. 5 is a top view of a central portion of an alternative second handpiece of the system of FIG. 1.
Figure 7:
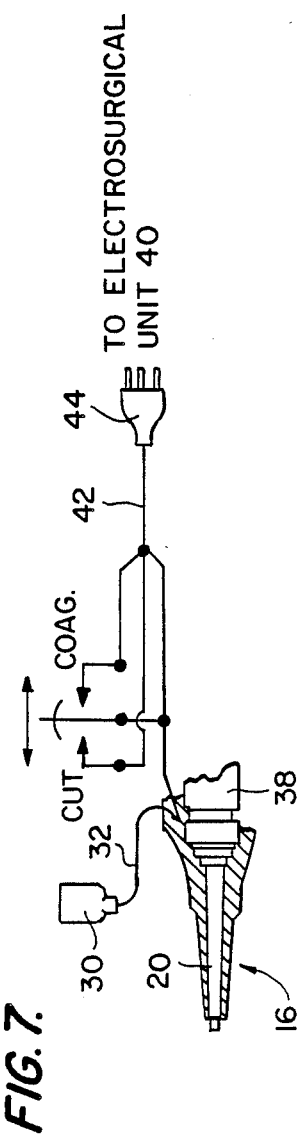
FIG. 7 is a side view of the forward portion of the second handpiece of FIG. 5 illustrating in schematic form an RF switching mechanism therefor.

A first embodiment of the electrical connector is a metallic acoustic vibrator which contains a laminated nickel alloy structure and is shown at 38 in FIG. 3. A second electrical connector embodiment 59 is to utilize a fluid conductive medium such as the saline irrigating solution of the irrigating system required by normal operation of the system. This conductive medium directly surrounds the tip 22 and can also provide electrical contact between the metallic contactor 58 and the tip as illustrated in FIGS. 5–7. This saline electrical fluid path does not interject mechanical loading of an acoustic vibrating member within the handpiece 16, as does the first embodiment.

To complete the RF electrical loop a dispersive ground pad 60 is provided as shown in FIG. 1 to be placed on the patient 14. See. e.g. U.S. Pat. No. 4,038,984. A cable 62 connected to the pad at one end and having a plug 64 at its other end (see also FIGS. 4 and 7) connects the pad to the ESU 40 when the plug 64 is plugged into the dispersive electrode jack 66 thereof. To provide proper operation of the electrosurgical features of this invention and in a conventional manner the RF current flows from the tip 22 through the patient 14, to the ground pad and back to the ESU 40, to complete the electrical loop.

At the first demonstration of bleeding during an ultrasonic tissue fragmenting procedure the damage blood vessel can thus be cauterized nearly instantaneously with a flick of the switch. Further, this system when in its cauterizing mode allows cautery to be applied directly by the ultrasonic tip 22 to cauterize bleeders in a similar manner as with standard neurosurgical techniques. Burning of the tip 22, charring of tissue and clogging of the aspiration tip 22 are not problems with these designs.

Tests have proven the effectiveness of this surgical system 10. In a moderate coagulation procedure coagulation was controlled with much less tissue charring than experienced with standard electrosurgical techniques. In an ultrasonic fragmentation and coagulation combination procedure enhanced fragmentation and controlled hemostasis were also observed. In an ultrasonic fragmentation and electrosurgical cutting combination procedure, enhanced fragmentation and controlled cutting were observed. And in an ultrasonic fragmentation and blend (cut and coagulation) electrosurgical procedure, enhanced surgical efficacy over any individual mode resulted and basic surgical characteristics of an ultrasonic surgical aspiration device were still retained. By adding RF energy to a vibrating tip not only does the rate of tissue removal significantly increase, but tissue selectivity and tactile feedback are provided in the same surgical instrument. Further by minimizing the number of devices at the surgical site, visualization of the surgical field is maintained and safety during the procedure increased.

The invention may be embodied in other specific forms without departing from its spirit or essential characteristics. The present embodiments are, therefore, to be considered in all respects as illustrative and not restrictive, the scope of the invention being indicated by the claims rather than by the foregoing description and all changes which come within the meaning and range of the equivalents of the claims are therefore intended to be embraced therein.

What is claimed is:

1. A surgical apparatus for performing one or more surgical procedures at a surgical site on a patient comprising:
    a handpiece,
    a tool supported by said handpiece,
    said tool having a vibratable tool tip,
    an RF current means selectively operable for providing an RF current to said tool tip for allowing performance of an electrosurgical procedure at the surgical site,
    a vibrating means for ultrasonically vibrating said tool tip,
    said tool tip having a top opening,
    said tool having a tool passageway therethrough communicating with said tip opening, and
    an aspirating means for applying a suction pressure on said tool passageway for aspirating tissue particles and fluid at the surgical site through said tip opening through said tool passageway and away from the surgical site,
    said RF current means including a switching means for switching the RF current provided to said tool tip to at least an RF cutting current during ultrasonic vibration.
2. The apparatus of claim 1 including,
    said switching means being on said handpiece.
3. The apparatus of claim 2 including,
    said switching means being secured to and supported by said handpiece.
4. The apparatus of claim 3 including,
    said switching means being built into said handpiece.
5. The apparatus of claim 2 including,
    said switching means comprising a footswitch adapted to be operated by a foot of the operator of said handpiece.
6. The apparatus of claim 1 including,
    said switching means comprising a manifold secured to said handpiece and a switch assembly connected to said manifold and movable therewith when securing said manifold to or removing said manifold from said handpiece.
7. The apparatus of claim 6 including,
    said switch assembly being integrally formed with said manifold.
8. The apparatus of claim 1 including,
    said switching means comprising a nosecone securable onto said handpiece, a switch secured to said nosecone, and a cable means for operatively connecting said switch to an electrosurgical unit.
9. The apparatus of claim 8 including,
    said switching means including a securing means for securing said nosecone to said handpiece.
10. The apparatus of claim 1 including,
    said switching means comprising a push button switch assembly at said handpiece.
11. The apparatus of claim 1 including,
    said switching means comprising a rocker-type switch assembly at said handpiece.
12. The apparatus of claim 1 including,
    said switching means comprising a slide-type switch assembly at said handpiece.
13. The apparatus of claim 1 including,
    said switching means comprising a single pole double throw switch which is normally open.

14. The apparatus of claim 1 including,
said RF current being 500 KHz.
15. The apparatus of claim 1 including,
said RF cutting current being 500 KHz.
16. The apparatus of claim 1 including,
a connecting means for operatively connecting said handpiece to an electrosurgical unit which generates the RF current.
17. The apparatus of claim 16 including,
said connecting means including a selecting means for selecting between cutting and coagulating modes of the RF current to be delivered to said tip.
18. The apparatus of claim 1 including,
an irrigating means associated with said handpiece for providing irrigating fluid to the surgical site adjacent said tip.
19. The apparatus of claim 18 including,
said irrigating means including an irrigating fluid passageway at least a part of which is supported by said handpiece, and said passageway having a passageway exit port adjacent to said tip.
20. The apparatus of claim 1 including,
said RF current means including an electrosurgical unit for generating RF energy.
21. The apparatus of claim 20 including,
said electrosurgical unit being a stand-free unit and said RF current means including a cable electrically connecting said stand-free electrosurgical unit to said handpiece.
22. The apparatus of claim 1 including,
said RF current means including an acoustic vibrator component supported by said handpiece and operatively connectable to a source of RF energy.
23. The apparatus of claim 22 including,
a mechanical connecting means for operatively connecting said acoustic vibrator component to said tip.
24. The apparatus of claim 22 including,
a conducting fluid connecting means for operatively connecting said acoustic vibrator component to said tip.
25. The apparatus of claim 24 including,
said conducting fluid connecting means using a surgical site irrigating fluid for conducting the RF energy to said tip.
26. The apparatus of claim 1 including,
said RF current means including a generating means for generating the RF current,
said aspirating means including a suction means for generating the suction pressure, and
a housing means for housing together said generating means and said suction means.
27. The apparatus of claim 1 including,
said RF current means is operable for delivering RF current to said tool tip in an electorsurgical procedure on tissue at the surgical site while said vibrating means is ultrasonically fragmenting tissue at the surgical site.
28. The apparatus of claim 1 including,
said RF current means is operable for delivering to deliver RF current to said tool tip in an electrosurgical procedure on tissue at the surgical site while said aspirating means is aspirating tissue particles and fluid through said tip opening away from the surgical site.
29. The apparatus of claim 1 including,
said RF current means including a coupling means for electrically coupling said tool tip with an electrosurgical unit.
30. The apparatus of claim 29 including,
said RF current means including an electrical filtering means for preventing malfunctioning of the logic controls of said apparatus when said coupling means is coupling said tool tip with the electrosurgical unit and the electrosurgical unit is being activated.
31. The apparatus of claim 1 wherein:
said switching means is selectively operable to switch said RF current means to supply an RF cauterizing current.
32. The apparatus of claim 31 wherein: said switching means is selectively operable to provide a simultaneous blend of RF cutting and RF coagulating currents.
33. The apparatus of claim 32 wherein: said switching means is selectively operable to control said RF current to an inoperative condition independent of operation of said vibrating means.
34. The apparatus of claim 31 wherein: said switching means uses a saline type solution for connecting RF current to said tool.
35. The apparatus of claim 1 wherein:
said switching means is selectively operable to control said RF current means to an inoperative condition independent of operation of said vibrating means.
36. A method for conducting enhanced cutting at a surgical site on a patient comprising:
applying at least an RF cutting current to an operative tip of an ultrasonic surgical aspirating instrument,
ultrasonically vibrating the operative tip,
positioning the tip at the surgical site, and
thereafter, positioning the tip at the surgical site as needed as the RF cutting current is delivered by the tip to the surgical site.
37. The method of claim 36 including,
said applying step being before said positioning step.
38. The method of claim 36 including,
said positioning step being before said applying step.
39. The method of claim 36 including,
contacting a dispersive electrode to the patient to form part of an electrical loop with a source of the RF cutting current.
40. The method of claim 36 including,
performing ultrasonic fragmentation on tissue at the surgical site with the tip of the instrument.
41. The method of claim 40 including,
said performing step being while the RF current is being delivered through the tip to the surgical site.
42. The method of claim 36 including,
with the tip being positioned at the surgical site,
switching the instrument between an RF coagulating mode thereof and an RF cutting mode thereof.
43. The method of claim 33 including,
applying an RF coagulating current to the tip during said applying an RF cutting current step and delivering the blend current thereby produced to tissue at the surgical site.
44. The method of claim 36 including,
delivering via the tip the RF coagulating current in a dessication procedure for deep coagulation drying out of large volumes of tissue.
45. The method of claim 36 including, delivering via the tip the RF coagulating current in a fulguration procedure for spray coagulation for drying out the surface of tissue.

46. The method of claim 36 including,
supplying an irrigating fluid to the surgical site generally adjacent to said tip via fluid conduit supported by a handpiece.

47. A method for electrosurgically cutting tissue at a surgical site on a patient comprising:
applying an RF cutting or an RF coagulating current to an operative tip of an ultrasonic aspirating instrument,
ultrasonically vibrating the tip,
thereafter, positioning the tip at the site as needed, as the RF cutting current is delivered to the surgical site to perform the tissue cutting procedure,
with the tip being positioned generally at the surgical site, switching the instrument between an RF coagulating mode thereof and an RF cutting mode thereof.

48. The method of claim 47 including,
said applying step being before said positioning step.

49. The method of claim 47 including,
said positioning step being before said applying step.

50. The method of claim 47 including,
performing ultrasonic fragmentation on tissue at the surgical site with the tip of the instrument.

51. The method of claim 50 including,
said performing step being while the RF cutting current is being delivered through the tip to the surgical site.

52. The method of claim 47 including,
affixing a dispersive electrode to the patient to form part of an electrical loop with a source of the RF cutting current.

53. The method of claim 47 including,
while delivering the RF cutting current to the surgical site, aspirating tissue particles and fluid through an opening in the tip and away from the surgical site.

54. The method of claim 47 including,
supplying an irrigating fluid to the surgical site generally adjacent to the tip via a fluid conduit supported by a handpiece.

* * * * *